(12) United States Patent
Levine

(10) Patent No.: US 6,865,414 B1
(45) Date of Patent: Mar. 8, 2005

(54) APPARATUS AND METHOD FOR AUTOMATICALLY SENSING THRESHOLD HISTOGRAM WITH DIFFERENTIATION OF SINUS FROM ECTOPIC BEATS

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 383 days.

(21) Appl. No.: 09/961,121

(22) Filed: Sep. 20, 2001

(51) Int. Cl.[7] .............................................. A61B 5/0452
(52) U.S. Cl. ....................................................... 600/510
(58) Field of Search ................................ 600/508–510, 600/515, 516, 518, 519, 373, 374, 393

(56) References Cited

U.S. PATENT DOCUMENTS

| | | | |
|---|---|---|---|
| 4,766,902 A | | 8/1988 | Schroeppel ............ 128/419 PG |
| 4,768,511 A | | 9/1988 | DeCote, Jr. ............ 128/419 PG |
| 4,880,004 A | | 11/1989 | Baker, Jr. et al. ..... 128/419 PG |
| 5,050,599 A | | 9/1991 | Hoegnelid ............ 128/419 PG |
| 5,271,392 A | | 12/1993 | Ferek-Petric .................. 607/14 |
| 5,316,001 A | | 5/1994 | Ferek-Petric et al. .. 128/661.08 |
| 5,318,595 A | | 6/1994 | Ferek-Petric et al. ......... 607/17 |
| 5,339,820 A | | 8/1994 | Henry et al. ................ 128/696 |
| 5,348,021 A | | 9/1994 | Adams et al. .............. 128/708 |
| 5,370,124 A | | 12/1994 | Dissing et al. .............. 128/696 |
| 5,374,282 A | | 12/1994 | Nichols et al. ............... 607/18 |
| 5,455,115 A | | 10/1995 | Lubowitz et al. ......... 428/411.1 |
| 5,476,485 A | * | 12/1995 | Weinberg et al. ............. 607/28 |
| 5,560,369 A | * | 10/1996 | McClure et al. ............ 600/518 |
| 5,620,466 A | | 4/1997 | Haefner et al. ................ 607/5 |
| 5,713,928 A | * | 2/1998 | Bonnet et al. .................. 607/9 |
| 5,868,680 A | * | 2/1999 | Steiner et al. .............. 600/518 |
| 5,891,178 A | * | 4/1999 | Mann et al. .................. 607/27 |
| 6,112,119 A | * | 8/2000 | Schuelke et al. ............... 607/9 |

OTHER PUBLICATIONS

Levine, Paul A., M.D., FACC, "Guideline to the Routine Evaluation and Follow–up of the Implanted Pacing System", pp 1–58, (Jan. 1993).

Levine, Paul A., M.D., FACC, "The Importance of the Post–Ventricular Atrial Blanking (PVAB) with Respect to Far field R Wave Detection", PVAB and FFRW Management, pp 1–16 (Nov. 21, 1999).

Levine, Paul A., M.D., "Confirmation of Atrial Capture and Determination of Atrial Capture Thresholds in DDD Pacing Systems", Clin. Prog. and Electrophysiol, vol. 2, No. 5, pp 465–473 (1984).

Levine, Paul A., et al., "Assessment of Atrial Capture in Committed Atrioventricular Sequential (DVI) Pacing Systems", PACE, vol. 6, Part 1, pp 616–623 (May–Jun. 1983).

Fröhlig, Gerd, et al., "Bipolar Ventricular Far–Field Signals in the Atrium", PACE, vol. 22, pp 1604–1613 (Nov. 1999).

* cited by examiner

*Primary Examiner*—Jeffrey R. Jastrzab
*Assistant Examiner*—Frances P. Oropeza

(57) ABSTRACT

An implantable programmable cardiac stimulation device and associated method for differentiating between normal sinus events and ectopic beats. The stimulation device monitors the sensing thresholds of sinus and non-sinus cardiac events, and stores a history of these sensing thresholds along with temporal data for accurate event detection. The stimulation device further provides accurate and appropriate detection of sensed events including P-waves, non-conducted PACs, and conducted PACs and thus verifies correct detection of PVCs and R-waves. Furthermore, the present invention provides a history record of ectopic events, distinguished by sensing thresholds and timing intervals, giving a valuable diagnostic tool to the physician in optimizing rhythm management therapy. In addition, the stimulation device allows the sensitivity threshold to be set based on a single cardiac cycle and past history.

40 Claims, 7 Drawing Sheets

APPARATUS AND METHOD FOR AUTOMATICALLY SENSING THRESHOLD HISTOGRAM WITH DIFFERENTIATION OF SINUS FROM ECTOPIC BEATS

FIELD OF THE INVENTION

This invention relates generally to a programmable cardiac stimulation device for the purpose of differentiating between normal sinus events and ectopic beats. More specifically, the present invention is directed to an implantable stimulation device and associated method for automatically monitoring sensing thresholds of sinus and non-sinus cardiac events, and storing a history of these sensing thresholds along with temporal data for accurate event detection.

BACKGROUND OF THE INVENTION

Conventional pacemakers and ICDs require manual programming of numerous programmable parameters, including but not limited to: atrial sensitivity, ventricular sensitivity, post-ventricular atrial refractory period (PVARP), post-ventricular atrial blanking period (PVAB), and other parameters such as ventricular refractory period, ventricular output, atrial output, choice of pacing mode, upper rate limit, base rate, sleep rate, sensor slope, sensor threshold, and so forth. The programming of these parameters can be inaccurate and time consuming, and requires highly-skilled medical expertise to accomplish.

An added complication to the process of manually programming atrial or ventricular sensitivity is that signal amplitudes observed on EGM monitors in a clinical setting do not correlate well with the signal amplitudes sensed by the implanted pacemaker or ICD after the signal has been processed by internal circuitry which includes various filters and amplifiers. Attempts to automate programming of sensitivity have not been completely successful, in part because of the natural fluctuation in the amplitudes of myopotentials and the incidence of noise associated with skeletal muscle depolarizations in unipolar systems and fluctuations in the amplitude of the intrinsic beats with marked differences between the sinus P wave and conducted ORS complex with respect to ectopic beats which cannot be assessed at the time of implantation or follow-up because they are not present at those times in both the unipolar and bipolar sensing configurations.

Selecting appropriate atrial sensitivity can be particularly challenging due to the low amplitude of atrial events, the small differences between sinus atrial event amplitudes and ectopic atrial event amplitudes, and the desire to sense and accurately detect low level signals associated with atrial fibrillation, flutter or ectopic foci.

The importance of correctly programming atrial sensitivity, however, cannot be over emphasized. An incorrect high atrial sensitivity would predispose to over-sensing and inappropriate mode switching. An overly low atrial sensitivity would prevent the correct detection of atrial fibrillation and would result in inappropriate ventricular pacing during atrial fibrillation associated with sensing and triggering on the intermittent atrial signals of sufficient amplitude, with serious hemodynamic consequences. In addition, under-sensing of premature atrial contractions (PACs) and premature ventricular contractions (PVCs) can result in arrhythmia induction induced by competition.

The problem of automatically and accurately sensing P-waves and R-waves is even more pronounced when using an "A-V cross-chamber" electrode configuration, that is, an electrode configuration in which the stimulation device senses cardiac signals between an atrial tip electrode and a ventricular tip electrode, and stimulates each chamber in a unipolar fashion from the respective electrode to the housing (i.e., typically referred to as the case electrode). When such electrodes are implanted, various electrode sensing configurations are possible, e.g., atrial unipolar (A tip-case); ventricular unipolar (V tip-case): atrial-ventricular cross-chamber (A tip-V tip); ventricular unipolar ring (V ring-to-case), atrial unipolar ring (A ring-to-case), atrial bipolar (A tip-ring) or ventricular bipolar (V tip-ring).

While unipolar sensing configurations are more susceptible to extraneous noise, bipolar sensing configurations are also susceptible to problems of oversensing depending on electrode position and spacing.

Regardless of the cardiac event being sensed, and regardless of the electrode configuration being used, there is a need for an implantable device which is able to readily and reliably sense P-waves, R-waves, premature atrial contractions (PACs), and premature ventricular contractions (PVCs). The implantable device, if it is to perform its intended function, must correctly detect a sinus atrial depolarization (P-wave), a sinus-induced ventricular depolarization (R-wave), and it must not incorrectly detect a PVC or a PAC as a sinus P-wave or R-wave, or vice versa, and thus inappropriately adjust pacing parameters.

While it is well known that various blanking schemes may be used to block or blank out unwanted inappropriate physiologic signals such as far-field signals or retrograde P-waves by using different blanking intervals (i.e., PVARP, automatic PVARP extension, PVAB, etc.), and thereby prevent these far-field signals or retrograde P-waves from being falsely sensed as P-waves, such blanking schemes (based solely on timing considerations) have proven less than satisfactory because legitimate (anterograde) P-waves and PACs that need to be sensed, may and do occur during these blanking intervals.

A number of attempts have been made previously to provide accurate sensing and detection of cardiac events by incorporating an additional physiological signal to verify signal detection by the primary electrogram (EGM) sensing of the electrical events of the heart. An important limitation of this approach of adding a second physiological sensor is the added hardware required to implant in the patient and the additional circuitry required to interpret more than one physiological signal and relate them.

Other attempts to improve signal detection have focused on alternative approaches in processing the EGM signal by modifying the detection circuitry, thus avoiding additional sensor implantation. Various schemes have been proposed such as using two sense amplifiers receiving the same signal but possessing different sensitivity settings that are adjusted in; tandem, two comparators with different threshold detection levels, or more than one signal processing parameter (such as amplitude and slew rate).

A major limitation of these methods is that in order to make automatic adjustments to sensitivity, a stable rhythm is required. In essence, during sensitivity adjustments, the normal function of the sensing circuitry is interrupted momentarily. This circuitry is integral to the timing operations of the pacemaker or ICD which is why it is possible to first verify rhythm stability prior to initiating any threshold or sensitivity testing or adjustment. Thus, frequent premature beats or irregular rates might inhibit automatic sensing threshold tests and sensitivity adjustment and lead to prolonged periods of inappropriate sensing and even delivery of electrotherapies with adverse effects based on erroneous detections.

A further limitation of conventional devices is that the primary sensing circuitry is automatically adjusted such that only a target event of interest is detected, for example P-waves but not PACs. Such exclusive sensing eliminates the tracking of certain non-sinus events that are important to detect for proper pacemaker function and are of diagnostic interest to a medical practitioner.

Therefore, there is still an unsatisfied need to automatically monitor sensing thresholds of various cardiac events, such as P-waves and PACs, R-waves and PVCs, and to accurately detect and discriminate these events without interruption of the normal operation of the pacemaker. This need becomes particularly acute when sensing between inter-chamber electrodes, e.g., when sensing using an A-V cross-chamber electrode configuration.

SUMMARY OF THE INVENTION

The present invention addresses these needs by providing a programmable cardiac stimulating device and associated method that differentiate between normal sinus events and ectopic beats. The implantable stimulation device and associated method provide for the automatic monitoring of sensing thresholds of sinus and non-sinus cardiac events, and for the storage of a history of these sensing thresholds along with temporal data for accurate event detection.

It is another feature of the present invention to provide a method of automatically monitoring the sensing threshold of a sinus cardiac event as well as premature events without additional complex circuitry and without interruption of the normal function of the primary sensing circuitry integral to the timing operations of the pacing system.

Still another feature of the present invention is to provide a historical record of event sensing thresholds and timing relationships to be available to a medical practitioner during patient follow-up visits. As used herein, an event sensing threshold is the highest numerical sensitivity setting at which an event is repeatedly sensed. Further, it would be advantageous to store a history of detected events, both sinus and non-sinus distinguished by sensing threshold and timing relationships, to be available for diagnostic procedures such that optimal pacing therapy can be delivered.

The foregoing, and other features, are accomplished by a single or multi-chamber cardiac pacing device equipped with two sense amplifiers for a given channel. One sense amplifier acts as a primary sense amplifier and is used for sensing the cardiac chamber signal throughout normal device operation. The second sense amplifier is periodically used to monitor sensing threshold of one or more cardiac events occurring within a given chamber. For example, in the atrial channel, sensing threshold for P-waves as well as for one or more PACs can be determined. Sensing threshold is determined by progressively decreasing the sensitivity of the second sense amplifier until the event is no longer sensed. The lowest sensitivity at which an event is consistently sensed is the sensing threshold for that particular event. In another embodiment, a single primary sense amplifier may be used to search for sensing thresholds of sinus and ectopic events on a periodic basis.

The present invention further provides for differentiation between normal sinus events and premature complexes by comparing timing relationships of these events. If an event is repeatedly sensed at a given sensitivity and occurs at a regular time interval that is approximately equal to a running average of previously detected cycle intervals, it is detected as a sinus event, for example a P-wave. The sensitivity of the primary sense amplifier can then be automatically adjusted to the newly determined sensing threshold for ongoing reliable detection of the sinus event.

However, if the time interval is irregular, or a given amount shorter than the running average, the event is detected as a premature contraction, for example a PAC. The sensing threshold of the premature contraction is then stored in memory. If PACs are frequent, the present invention allows for discrimination of more than one PAC from sinus P-waves based on sensing threshold and timing relationships. These distinguishing characteristics are stored in memory in the form of a histogram.

Furthermore, a method is provided by which PACs conducted to the ventricle can be distinguished from normal P-R complexes or PVCs. A high incidence of PVC detection in the ventricular channel triggers a search in the atrial channel for an atrial event immediately preceding the PVC. If an atrial event is sensed at a regular interval prior to the PVC, the PVC is reclassified as an R-wave, and a determination is made based on timing relationships whether the atrial event is a P-wave or a conducted PAC by comparing the coupling interval between the atrial sensed event and the R-wave versus an average P-R interval.

The present invention thus clearly accomplishes several objectives, among which are the following: 1) automatic monitoring of sensing threshold and adjustment of the sensitivity settings that can be accomplished, in one embodiment, without interrupting the function of a primary sense amplifier integral to the timing operations of the stimulation device; and 2) it provides a histogram record containing sensing thresholds of P-waves, PACs, and the coupling interval for conducted PACs.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
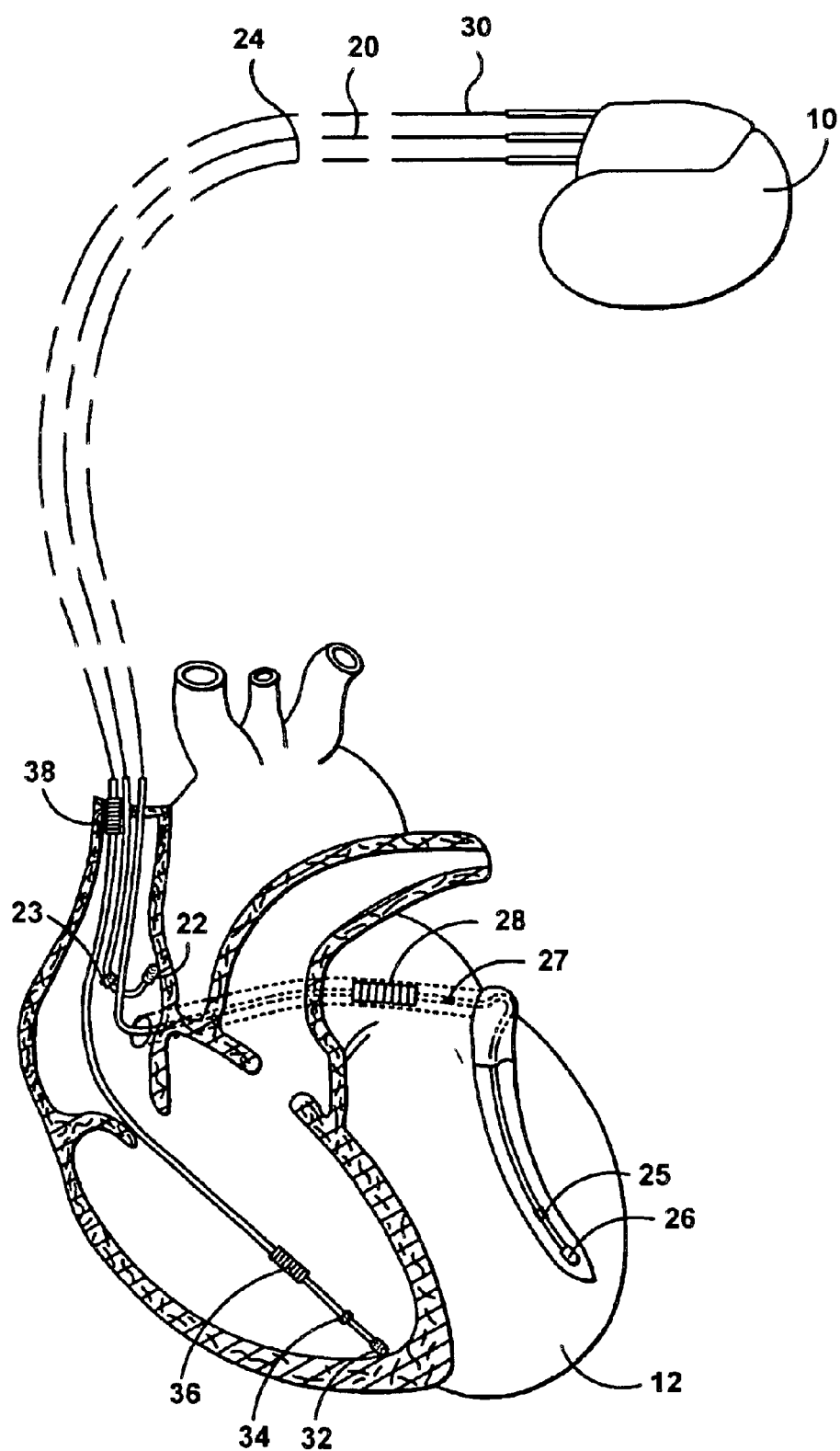
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have a right atrial ring electrode 23 to allow bipolar stimulation or sensing in combination with the right atrial tip electrode 22.

To sense left atrial and ventricular cardiac signals and to provide left-chamber pacing therapy, the stimulation device 10 is coupled to a "coronary sinus" lead 24 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. In an alternative embodiment, the coronary sinus lead 24 may also include a left ventricular ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
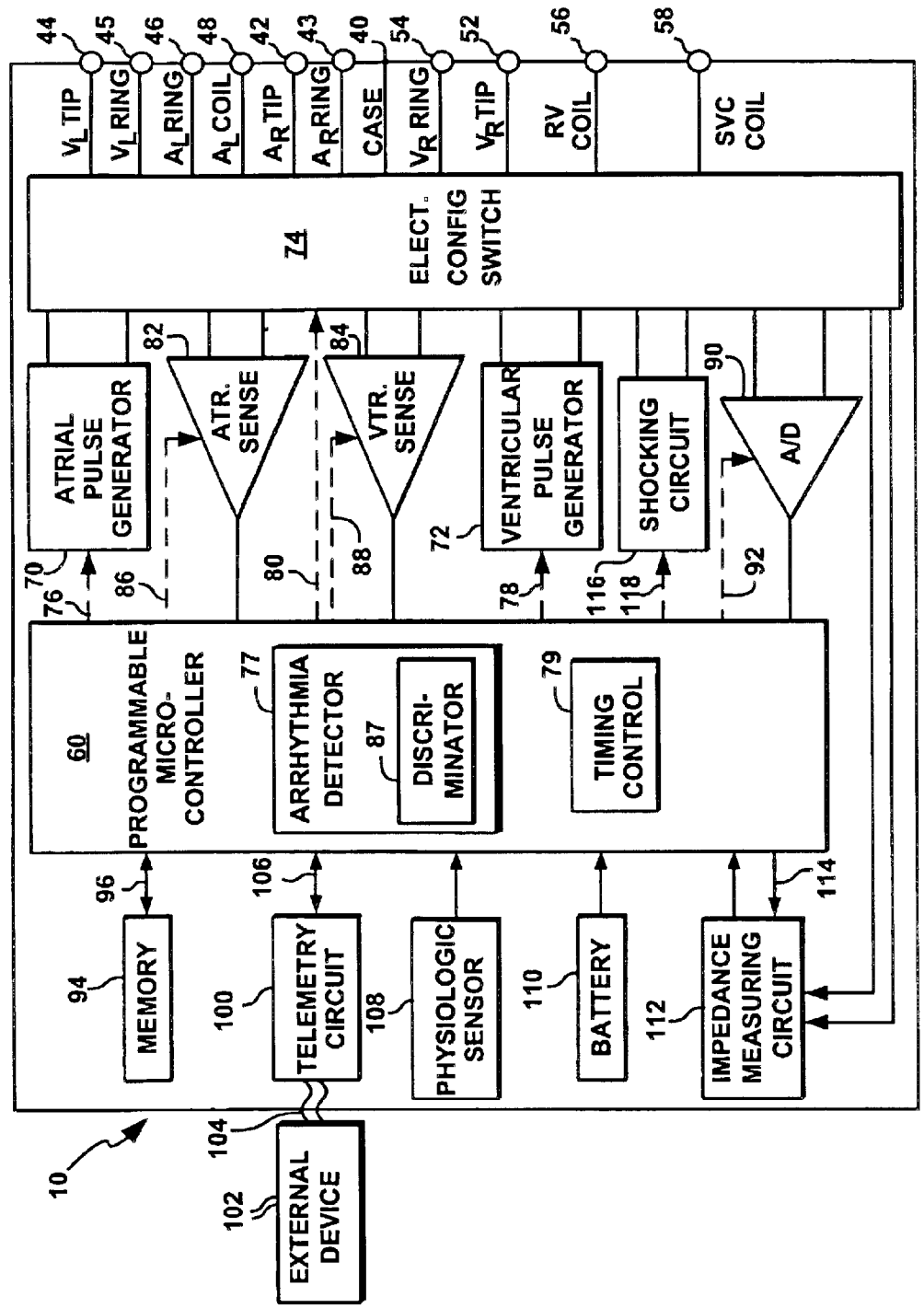
FIG. 2 is a functional block diagram of the multi-chamber stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The stimulation device 10 further includes a connector having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial ($A_R$) tip electrode 22. The connector may also include a right atrial ring terminal (AR RING) 43 for connection to the atrial ring electrode 23, and a left ventricular ring (VL RING) 45 for connection to the left ventricular ring electrode 25.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy.

The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and/or automatic gain control, bandpass filtering capability, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84. In accordance with the present invention, control signals from the microcontroller 60 initiate and execute specific algorithms that involve automatic adjustment of one or more sense amplifiers contained within the atrial and ventricular sensing circuits 82 and 84 for periodically monitoring sensing thresholds and discriminating sinus from non-sinus events, as will be described later in detail.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and Atrial Tachycardia or AT, high rate organized atrial rhythm (Atrial Flutter abbreviated Afl) and fibrillation rate zones in both the atrium and ventricle) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

In accordance with the present invention, the microcontroller 60 has the capacity to maintain running averages of timing intervals associated with detected sinus events such as P-to-P intervals (PPI), P-to-R intervals (PRI) and R-to-R intervals (RRI). These average intervals will be used by the methods of the present invention in distinguishing sinus from ectopic events, as will be fully described below.

Cardiac signals are also applied to the inputs of an analog-to-digital (AND) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the stimulation device 10 is the ability to sense and store a relatively large amount of data (e.g. from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses.

While the physiologic sensor 108 is shown as being included within the stimulation device 10, it is to be understood that the physiologic sensor 108 may alternatively be external to the stimulation device 10, yet still be implanted within, or carried by the patient A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood or other tissue, respiration rate and/or minute ventilation, pH of blood, ventricular gradient, etc. However, any sensor may be used which is capable of sensing a physiological parameter which corresponds to the exercise or metabolic status of the patient.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected.

The stimulation device 10 further includes a magnet detection circuitry, coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 by a control signal 114. The impedance measuring circuit 112 is advantageously coupled to the switch bank 74 so that any desired electrode may be used.

It is a function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patients heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 540 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
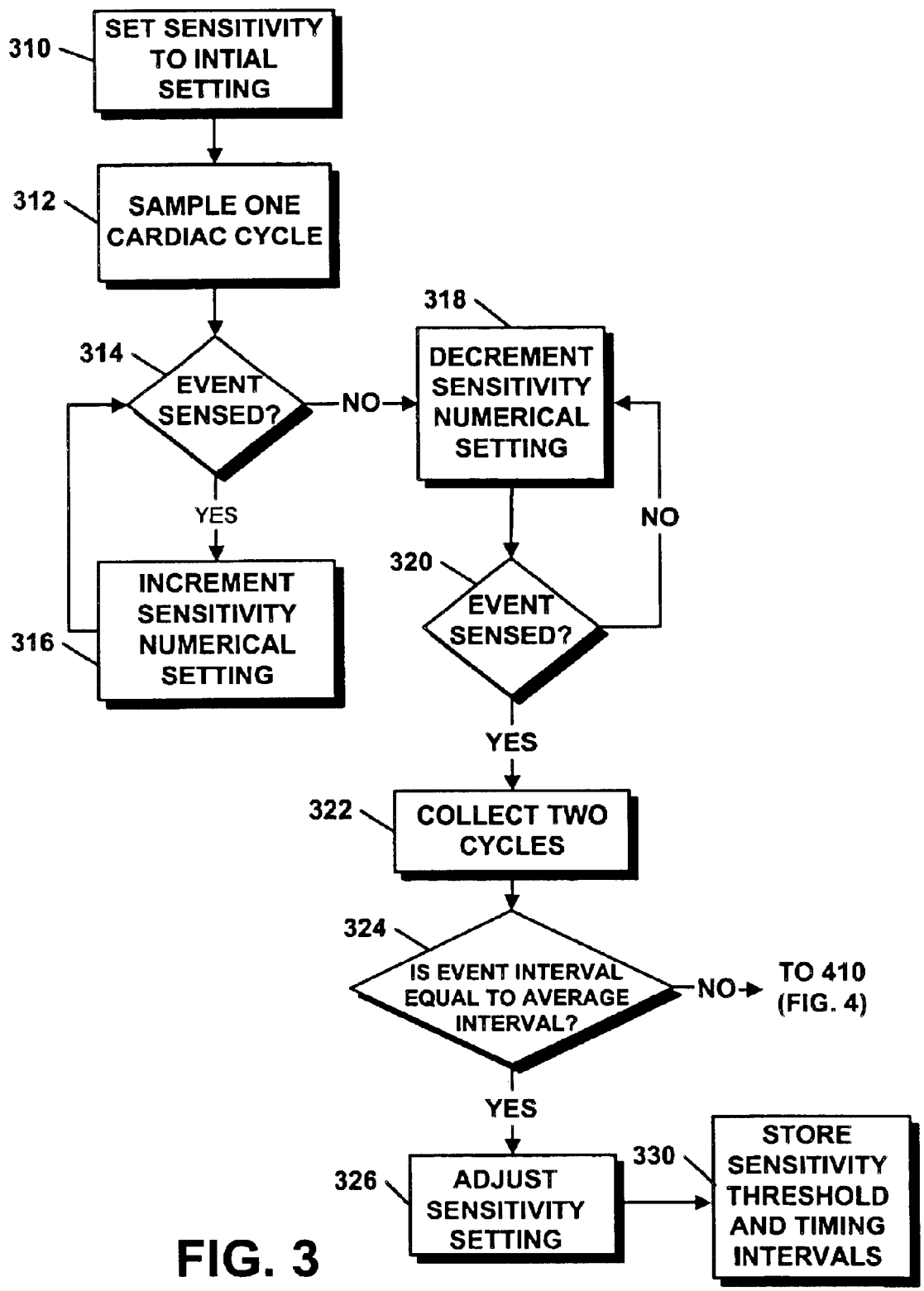
FIG. 3 is a flow chart depicting the method used by the stimulation device of FIG. 2 for determining sensing threshold according to a preferred embodiment of the present invention.

In FIG. 3, a flow chart is shown describing an overview of the operation and features implemented in one embodiment of the stimulation device 10. In this flow chart, and the other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device.

In this embodiment, the control program is comprised of multiple integrated program modules, with each module bearing responsibility for controlling one or more functions of the stimulation device 10. For example, one program module may control the delivery of stimulating pulses to the heart 12, while another may control the verification of ventricular capture and ventricular pacing energy determination. In effect, each program module is a control program dedicated to a specific function or set of functions of the stimulation device 10.

In particular, a program module is implemented by the stimulation device 10 to periodically monitor sensing threshold in accordance with the present invention. FIG. 3 is a flow diagram that illustrates a method 300 for automatically monitoring the sensing threshold of either atrial or ventricular events according to the present invention. The method 300 is initiated periodically by a control program executed by the microcontroller 60. For example, the method 300 might be initiated hourly, daily, weekly, and so forth. This periodicity is preferably programmable such that it could be tailored to the individual patient's need. Alternatively, the periodicity can be determined automatically by the microcontroller 60 based upon rhythm stability.

The method 300 begins at step 310 by setting the sensitivity of a sensing circuit, either the atrial sensing circuit 82 or the ventricular sensing circuit 84, to an initial setting.

At step 312, a cardiac cycle is sampled, and at decision step 314 the method 300 determines if a cardiac event is sensed. If an event is sensed, the sensitivity of the sensing circuit, either atrial sensing circuit 82 or ventricular sensing circuit 84, is decreased for the next cardiac cycle, such as by incrementing the numerical setting by one programming step.

If an event is again sensed at decision step 314, the sensitivity is again decreased at step 316 by increasing the numerical setting until the event is no longer sensed.

If at decision step 314 method 300 determines that an event is not sensed, it decreases the numerical setting, at step 318, back to the previous sensitivity at which the event was last sensed. This sensitivity setting at which an event is repeatedly sensed is considered the sensing threshold for the sensed event. Event sensing is re-verified at step 320, a and at step 322 a minimum of two cardiac cycles are collected to allow determination of the time interval between the two sensed events. This event interval is compared to the average interval measured between previously sensed sinus events, either an R-to-R interval or "RRI" or a P-to-P interval or "PPI", at decision step 324. The RRI or PPI is a running average determined by the microcontroller 60 based on R-wave or P-wave detection occurring on the ventricular sensing circuit 84 or atrial sensing circuit 82, respectively. If the event interval is approximately equal to the average sinus interval, then sinus event detection is confirmed with the sensitivity of the appropriate sensing circuit 82 or 84 being adjusted according to the sensing threshold, at step 326, for consistent R-wave or P-wave detection thereafter. The sinus event sensing threshold and the timing intervals are logged in corresponding histogram bins at step 330.

Thus, a method is provided by which the atrial or ventricular sensing threshold for sinus events is automatically monitored and the sensitivity setting for sensing sinus events is automatically adjusted.

Figure 4:
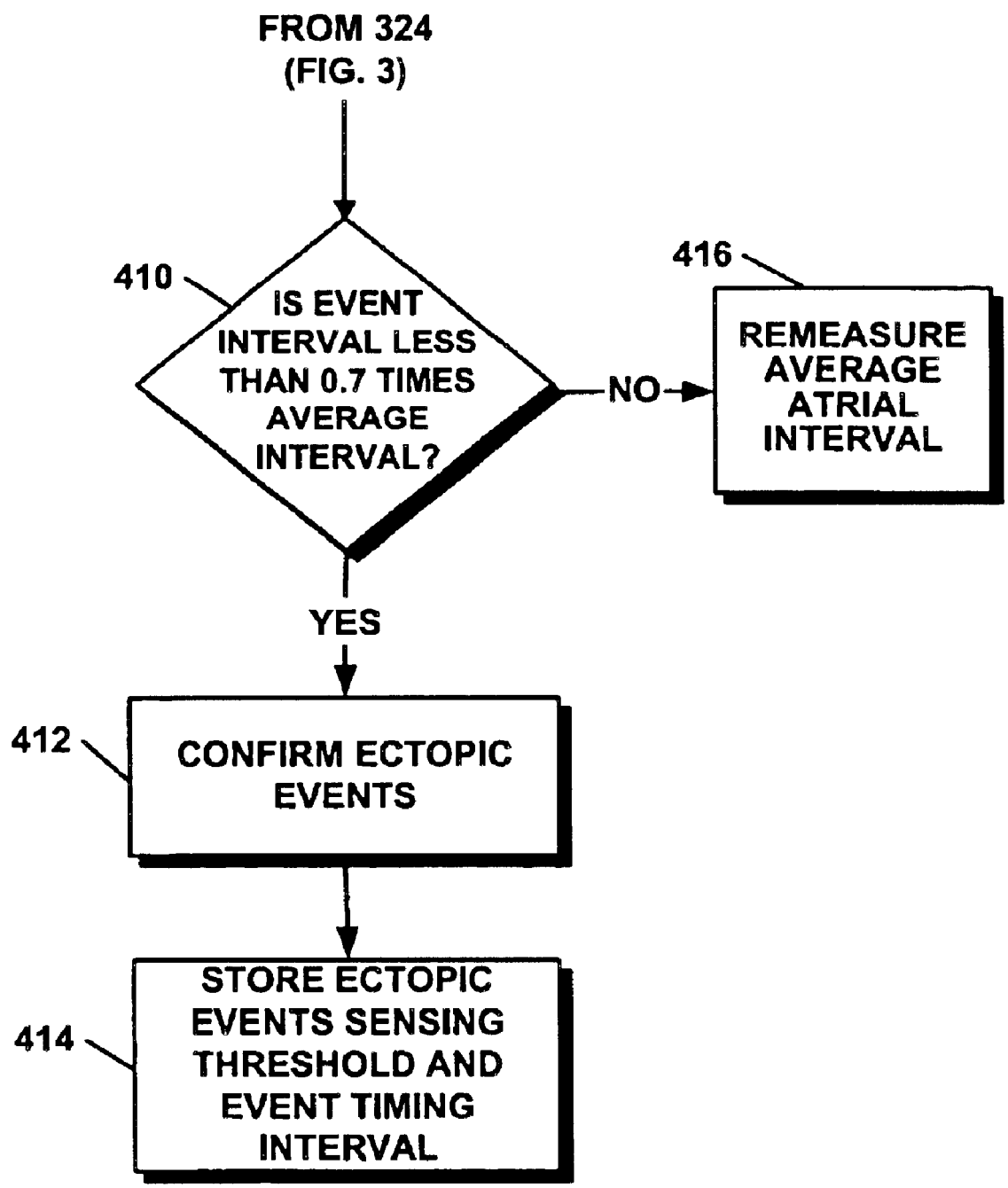
FIG. 4 is a flow chart depicting the method used by the stimulation device of FIG. 2 for discriminating non-sinus events from sinus events and accumulating histogram data according to a preferred embodiment of the present invention.

Referring again to decision step 324, if the event interval is not approximately equal to the average sinus interval, that is there is no substantial rhythm stability, the method 300 calls upon method 400 of FIG. 4 for determining whether the sensed event is a premature contraction (or ectopic beat) rather than a sinus P-wave or R-wave.

The first step of method 400 is to compare the event interval determined in method 300 to some percentage, for example 70%, of the average sinus interval, either the P-to-P interval or the R-to-R interval, at decision step 410. This percentage is preferably a programmable value. Alternatively, the event interval could be compared to a fixed time interval.

If the event interval is less than the defined percentage of the average sinus interval, the premature contraction detection (either premature atrial contraction or premature ventricular contraction) is confirmed at step 412. The current sensitivity setting is stored in memory 94 (FIG. 2) as the sensing threshold for the premature contraction, and the average time interval associated with the premature contraction, e.g., between a previous sinus event (P-wave or R-wave) and the premature contraction (PAC or PVC, respectively) is stored in a histogram bin assigned to the sensing threshold at step 414.

If at decision step 410, the event interval is not found to be less than the programmed percentage of the sinus interval, then method 300 triggers a redetection of the average sinus interval by the microcontroller 60 at step 416. A sensed but nonclassifiable event is logged in memory 94, for example in a sinus rate bin. Another possibility would be to log the event in a rate and amplitude matrix. Hence, for a given rate bin there may be a spectrum of signals at different amplitudes. This information is also valuable when the stimulation device 10 is programmed, to recognize the smallest amplitude signal.

Now that the sensing thresholds of the sinus and non-sinus events are determined and stored at steps 330 (FIG. 3) and 414 (FIG. 4), respectively, the stimulation device 10 uses the relative amplitude of complexes in the histogram bins to differentiate the premature or ectopic non-sinus events from the dominant rhythmic sinus complexes, provided there are two or more distinct peak sensing thresholds, A and B, in the histogram. Sensing threshold A refers to sinus events, while sensing threshold B refers to non-sinus events. As a result, when a signal is sensed at a sensitivity that is substantially equal to sensing threshold A, the signal is considered to be a sinus event. On the other hand, if a signal is sensed at a sensitivity that is substantially equal to sensing threshold B, the signal is considered to be a non-sinus event.

Figure 5:
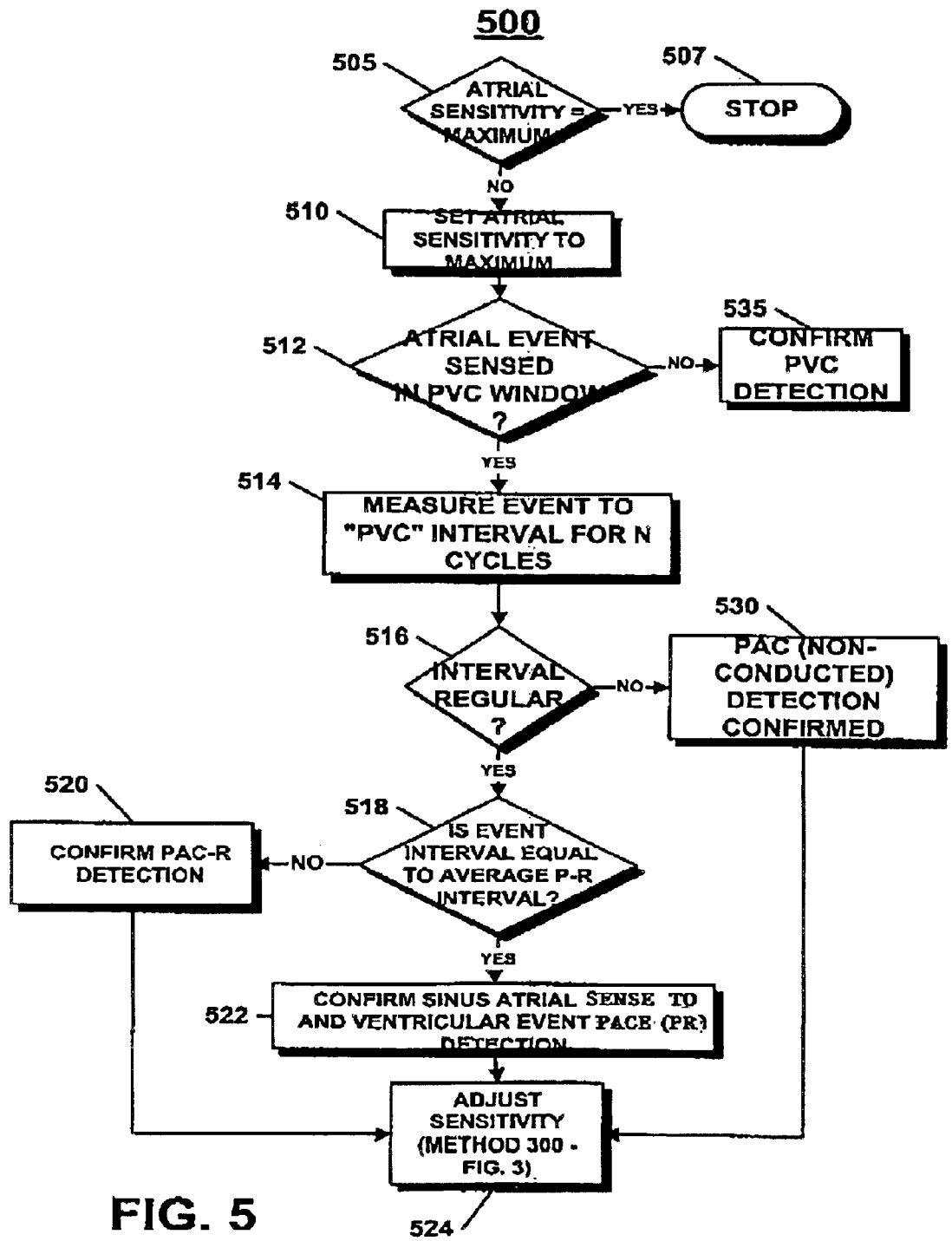
FIG. 5 is a flow chart depicting an additional mode of operation of the stimulation device of FIG. 2 for discriminating R-waves from PVCs by detecting preceding conducted PACs or sinus P-waves according to a preferred embodiment of the present invention.

Another method of operation 500 included in the present invention is illustrated by the flow chart of FIG. 5. The method 500 provides an algorithm for verifying the detection of PVCs versus R-waves resulting a from conducted atrial events. When no atrial event is detected prior to a ventricular sensed event, the ventricular event is detected as a PVC. However, if the atrial sensitivity is too low (a high numerical setting), an atrial event, either a sinus P-wave or a PAC, that is conducted to the ventricle could cause ventricular depolarization, yet be undetected in the atrial channel. Hence, an inappropriate PVC detection is made by the ventricular channel instead of an R-wave detection.

In the present invention, the microcontroller 60 monitors the frequency of PVC detections in the ventricular channel. The microcontroller 60 triggers the method 500 when the number of PVC detections exceeds a pre-defined limit within a given time period, for example 10 PVC detections in one hour. The number of PVC detections and the time interval in which they are detected could be fixed or, preferably, programmable values.

Once initiated, the method 500 first checks if the atrial sensitivity is equal to the maximum atrial sensitivity available (i.e., the lowest numerical value) at decision step 505. If the atrial sensitivity is already at the most sensitive setting, the method 500 is aborted at termination step 507. If not, the atrial sensitivity is set to the maximum atrial sensitivity available (lowest numerical setting) at step 510. The microcontroller 60 then defines a window of time in which to "look" for an atrial event immediately preceding the detected PVC (step 512). If no atrial event is sensed, the method 500 confirms PVC detection at step 535.

On the other hand, if an atrial event is sensed, the ventricular detected "PVC" is likely to be an R-wave following either a sinus P-wave or a conducted PAC that was previously not detected by the atrial channel due to undersensing. To determine if the sensed atrial event is a P-wave or conducted PAC, the time interval between the newly sensed atrial event and the detected "PVC" is measured for a given number of cycles, for example 5 cycles, at step 514. It is also possible to allow atrial events occurring within the PVARP and further within a programmable window preceding the detected R-wave, to cause the R-wave to be labeled as a sinus R-wave rather than a PVC. This will also allow a more accurate labeling of the sensed R-wave as a PVC or as a conducted event.

At step 516, the regularity of the time intervals between the atrial event and the detected "PVC" is determined. For example, the average and standard deviation of five measured intervals could be calculated. If the standard deviation is less than some minimum percentage of the average, the intervals are considered regular. Otherwise, the intervals are considered "not regular". If the intervals are not regular, the atrial event is confirmed as a detected but non-conducted PAC (step 530), and the PVC detection remains confirmed.

As used herein, a non-conducted PAC is a PAC event that was not conducted to the ventricle and that does not cause an R-wave depolarization. For example, if the interval from a sensed event in the atrium and the detected PVC, is irregular, then the atrial sensed event is categorized as a PAC that is not conducted to the ventricle. Therefore, it is a detected PAC but non-conducted. Since it is non-conducted, the "PVC detection" remains correct.

However, if the interval between the sensed event in the atrium and the detected "PVC" is regular, then the detected PAC is actually a conducted PAC that is causing a ventricular depolarization, or R-wave. The previous "PVC detection" in the ventricle is therefore erroneous, and it is now reclassified as an R-wave resulting from the conducted PAC. Thus, the two events together are confirmed as a PAC-R detection. Alternatively, the two events can be classified separately as follows: a PAC detection is confirmed and an R-wave detection is confirmed.

More specifically, with reference to FIG. 5, if the intervals are regular, the PVC is reclassified as an R-wave. If the average event interval is approximately equal to a previously determined average P-R interval (PRI) as determined at decision step 518, then PR detection is confirmed at step 522. As used herein, PR detection refers to the detection of the P-wave and the subsequent R-wave. The PRI is a running average determined by the microcontroller 60 based on P-wave and R-wave detection by the atrial sense circuit 82 and ventricular sense circuit 84 during normal operation of stimulation device 10.

If the interval between the sensed atrial event and the PVC is regular and approximately equal to PRI, then the sensed event is classified as a P-wave (now a detected P-wave). The P-wave is naturally conducted to the ventricle causing a depolarization or R-wave, so the two events are confirmed as a detected P-wave and a detected R-wave, or PR detection.

A discriminator 87 could form part of the arrhythmia detector 77 to monitor the PR, AR, AV, or PV intervals. A conducted ventricular complex would result in a stable PR or AR rhythm at other times. If the predominant complexes are AV or PV, then the coincidence of a P wave followed by an "R" wave or an atrial output followed by an "R" wave is actually a late cycle (slow rate) PVC. For these cycles, the atrial event-R-wave interval will be shorter than the AV, PV or even AR or PR interval, as it would be unusual for the native AV conduction to spontaneously and abruptly shorten.

Once a PR detection is made, method 500, at step 524, calls upon method 300 of FIG. 3 to perform an automatic sensing threshold test and to reset the atrial sensitivity to a higher sensitivity for reliable P-wave sensing and detection, and subsequently accurate R-wave recognition.

Referring again to decision step 518, if the event interval, is not approximately equal to the PRI, the atrial sensed event is detected as a conducted PAC. Because the PAC is conducted to the ventricles, it is followed by an R-wave, which had previously been misclassified as a PVC prior to proper PAC detection. Thus, PAC-R detection can now be correctly confirmed at step 520.

Method 500 then calls upon method 300 to perform a sensing threshold test to determine the sensing threshold of this particular PAC. This is accomplished by limiting the sensing window in which to perform the threshold test of method 300. The sensing window is that set by the microcontroller 60 corresponding to the coupling interval of the PAC and the preceding detected event, P wave or R-wave.

Any atrial events sensed outside this time window are, for the time being, ignored. In this way, the sensing threshold of only the conducted PAC can be determined. Next, method 300 in turn calls upon method 400 (FIG. 4) to store the PAC sensing threshold and its distinguishing timing interval, in this case the average coupling interval (PAC to R-wave interval), in a histogram.

In this way, the methods of the present invention make it possible to store in memory 94 (FIG. 2) the sensing threshold and associated timing intervals for one or more conducted PACs by setting a temporary sensing window to be active during the method 300 that is distinctly associated with the coupling interval of each PAC.

This information, in addition to the sensing threshold and conduction time for sinus P-waves as well as sensing thresholds of non-conducted PACs, is stored in memory such that it is available to the physician in the form of a histogram at the time of patient follow-up. If sufficient memory is available, an electrogram template of each distinct PAC, as classified by its sensing threshold and coupling interval, may also be stored in memory 94.

A further feature of the present invention is a programmable option for automatic sensitivity adjustment of the sense amplifier in atrial sensing circuit 82 such that atrial ectopic events are sensed and detected in addition to sinus P-waves. If the frequency of ectopic events is above a defined rate, a control program in microcontroller 60 would adjust the atrial sensitivity SA based on the sensing thresholds of PACs stored in memory 94. Accurate sensing and detection of both sinus P-waves and conducted PACs would then be achieved. Reliable detection of these events would prevent inappropriate mode-switching during normal device operation due to undersensing and erroneous classification of R-waves as PVCs.

Figure 6:
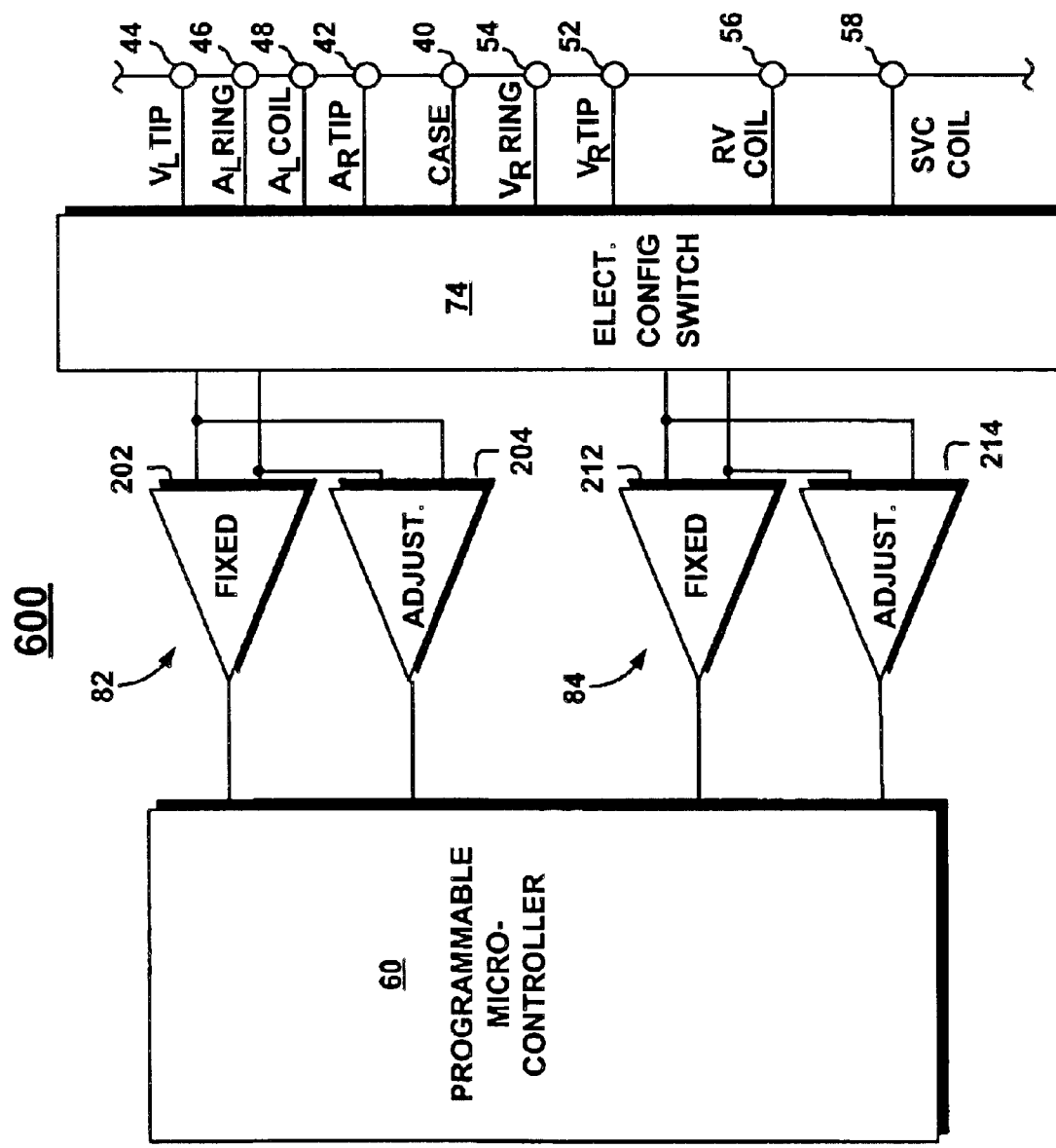
FIG. 6 is a partial functional block diagram of an alternative embodiment of the multi-chamber implantable stimulation device of FIG. 1, illustrating the use of two atrial sense amplifiers and two ventricular sense amplifiers.

FIG. 6 is a partial functional block diagram of another multi-chamber implantable stimulation device 600. The stimulation device 600 is generally similar in function and design to the stimulation device 10 of FIG. 2, and enables the monitoring of the sensing threshold rather than a pure signal amplitude. To this end, each of the atrial and/or ventricular channels includes two sense amplifiers. In the preceding embodiment, a single sense amplifier was used for the atrial or ventricular channel.

Two sense amplifiers allow for the implementation of a functional channel and a test channel. The functional channel remains at the programmed sensitivity while the test channel assesses the signal amplitude. If the signal amplitude is found to be close to the programmed sensitivity, then the system can either report this fact, recommend a change, or actually institute a change to the functional sense amplifier.

Considering now the atrial sensing circuit 82 of the atrial channel, it is comprised of two low power, precision sense amplifiers 202 and 204. One of these sense amplifiers (i.e., 202) is integral to the stimulation device 600 timing at its programmed setting (e.g., 1.0 mV). The second sense amplifier (i.e., 204) automatically adjusts its sensitivity on sequential complexes. Each change would be by one programming step, and is carried out on a periodic basis that might be programmable or dependent upon the stability of the patient's rhythm.

Similarly, the ventricular sensing circuit 84 of the ventricular channel, is comprised of two low power, precision sense amplifiers 212 and 214. One of these sense amplifiers (i.e., 212) is integral to the stimulation device 600 timing at its programmed setting (e.g., 1.0 mV). The second sense amplifier (i.e., 214) automatically adjusts its sensitivity on sequential complexes. Each change would be by one programming step, and is carried out on a periodic basis that might be programmable or dependent upon the stability of the patient's rhythm.

Each of the atrial and ventricular sense amplifiers 202, 204, 212, and 214 has a programmable gain and/or automatic gain control or automatic sensitivity control bandpass filtering capability, and a threshold detection circuit, to selectively sense the cardiac signal of interest.

Figure 7:
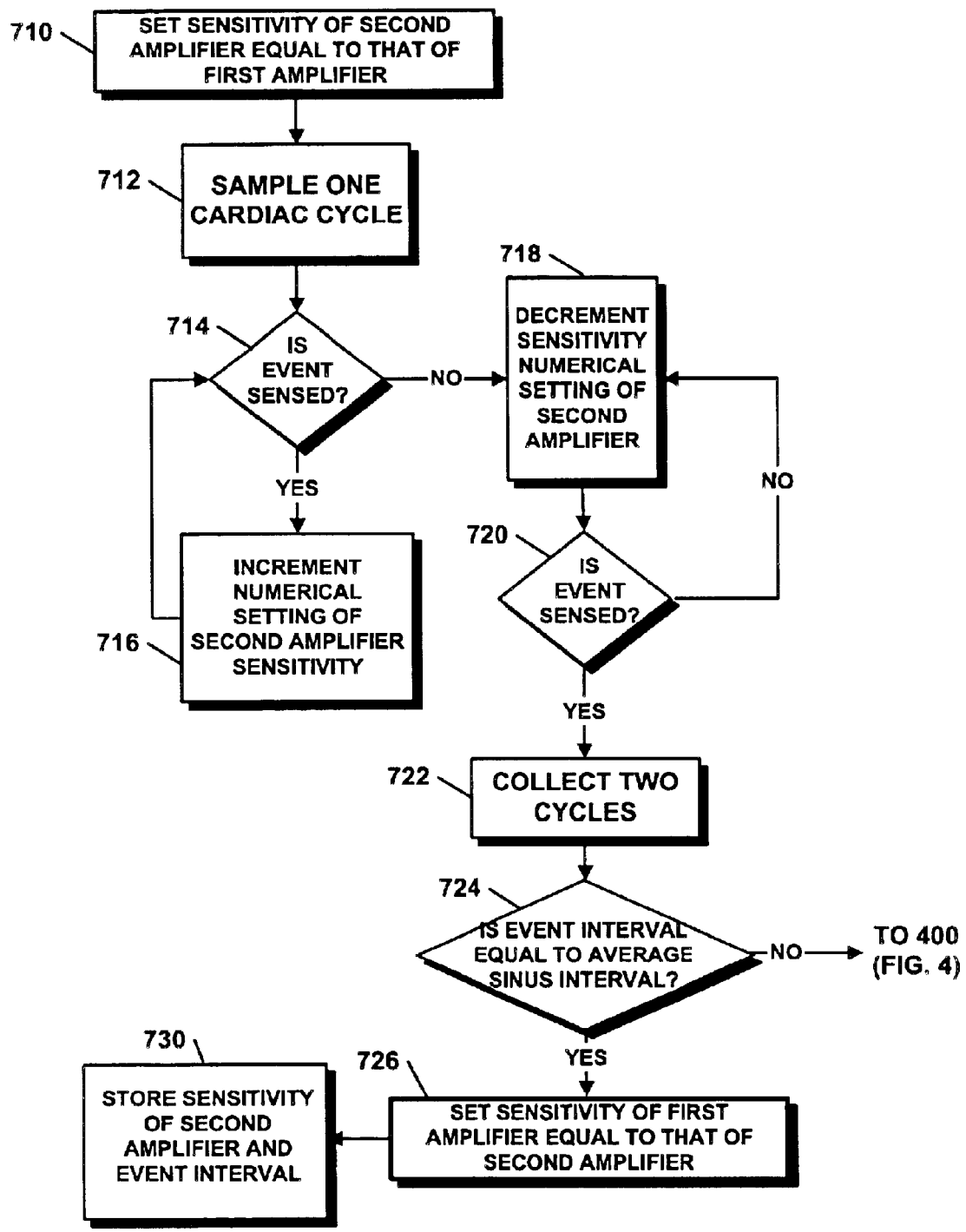
FIG. 7 is a flow chart depicting an alternative method used by the stimulation device of FIG. 6 for determining sensing threshold.

FIG. 7 illustrates a flow chart that depicts an alternative method 700 used by the stimulation device 600 of FIG. 6 for determining the sensing threshold of sinus and ectopic events. Though the method 700 will now be described with reference to the atrial channel, it should be understood a that this method is equally applicable to the ventricular channel.

The method 700 begins at step 710 by setting the sensitivity, S2, of the second sense amplifier 204 equal to the sensitivity, S1, of the first sense amplifier 202. The sensitivity of the first sense amplifier 202 is not adjusted at this time so as to preserve normal device operation while the method 700 continues.

At step 712, an atrial cardiac cycle is sampled, and at decision step 714 the method 700 determines if an atrial event was sensed. If an atrial event was sensed, the sensitivity, S2, of the second sense amplifier 204 is decreased for the next cardiac cycle, that is its numerical setting is incremented by one programming step. If the atrial event was again sensed at decision step 714, the sensitivity numerical setting, S2, of the second sense amplifier 204 is again incremented, at step 716, until the event is no longer sensed.

Thereafter, the sensitivity numerical setting, S2, of the second sense amplifier 204 is decremented, at step 718, back to the previous sensitivity at which the event was last sensed.

Event sensing is re-verified at step 720, and at step 722 a minimum of two cardiac cycles are collected to allow determination of the time interval between the two sensed events. This event interval is compared to the average interval measured between previously sensed P-waves, PPI, at decision step 724. PPI is a running average determined by microcontroller 60 based on P-wave detection occurring on the primary sense amplifier of the atrial sensing circuit 82.

If the event interval is approximately equal to PPI, then P-wave detection is confirmed with the numerical setting, S2, being the new sensing threshold for consistent P-wave detection thereafter. Thus, the sensitivity numerical setting, S1, of the first sense amplifier 202 is set equal to the sensitivity numerical setting, S2, of the second sense amplifier 204 at step 726. The sensitivity numerical settings S1, S2, and the event intervals are logged in corresponding histogram bins at step 730. As an optional feature, the automatic adjustment of the sensitivity numerical setting, S1, of the first sense amplifier 202 could be disabled, and the sensing threshold result (S2) only logged to memory such that the result is available during clinical follow-up visits.

If, upon initiation of the method 700 no event is sensed at the initial sensitivity numerical setting, (equal to S1), at the decision step 714, the sensitivity, S2, of the second sense amplifier 204 is increased, that is the numerical setting of the sensitivity S2 is decremented by one programming step. If still no atrial event sensing occurs as determined at decision step 720, the method 700 continues to decrement the sensitivity S2 (step 718) until an atrial event is sensed. Thereafter, a minimum of two cycles are collected at step 722 so that the event interval can be determined and then compared to PPI (step 724).

If the event interval does approximately equal PPI, P-wave detection is confirmed, and the sensitivity numerical setting, S1, of the first sense amplifier 202 is automatically decreased to the sensitivity, S2, of the second sense amplifier 204, and is set as the new sensing threshold for consistent P-wave detection. Therefore, the method 700 provides a way to automatically monitor the sensing threshold without interruption of the normal timing processes of the simulation device 600 (FIG. 6) that are based on the primary atrial sense amplifier 202 of the atrial sensing circuit 82.

Thus, an implantable cardiac device and method for determining rhythm stability and for reliably monitoring sensing threshold and automatically adjusting sensitivity settings according to a sensing threshold is provided. The present invention further provides accurate and appropriate detection of sensed events including P-waves, non-conducted PACs, and conducted PACs and further verifies correct detection of PVCs and R-waves.

Furthermore, the present invention provides a history record of ectopic events, distinguished by sensing thresholds and timing intervals, giving a valuable diagnostic tool to the physician in optimizing rhythm management therapy. In addition, the present invention allows the sensitivity setting to be set based on a single cardiac cycle and past history. One skilled in the art will appreciate that the present invention can be practiced by other than the described embodiments, which are presented for the purposes of illustration and not of limitation. The descriptions provided herein are for the sake of illustration and are not intended to be exclusive.

What is claimed is:

1. A method for use in a cardiac stimulation device to differentiate between sinus events and ectopic events, comprising:

sensing sinus events and ectopic events;

automatically determining sensing thresholds of the sinus events;

automatically determining sensing thresholds of the ectopic events;

storing the sensing thresholds of the sinus events, the sensing thresholds of the ectopic events, and timing relationships that define sinus intervals and ectopic intervals;

classifying a sensed cardiac event as a sinus event or an ectopic event based on the proximity of an amplitude of the cardiac event to any of the sensing thresholds of the sinus events or the sensing thresholds of the ectopic events; and classifying a sensed cardiac event as a sinus event or an ectopic event based on the proximity of the sensed cardiac event to a previous average cycle length in a corresponding cardiac chamber.

2. The method according to claim 1, wherein the step of automatically determining sensing thresholds of the sinus events comprises:

adjusting a sensitivity setting until an event sensing threshold is determined; and determining the sinus event sensing thresholds on a rhythmic consistency of occurrence of the sensed events.

3. The method according to claim 2, wherein the step of automatically determining sensing thresholds of the ectopic events comprises determining the ectopic event sensing thresholds on any one of:

a lack of rhythmic consistency of occurrence of sensed events, and a rhythmic consistency that is shorter in time than sinus event sensing.

4. The method according to claim 3, wherein the step of adjusting a sensitivity setting comprises maintaining a sensitivity setting of a first sense amplifier, while adjusting a sensitivity setting of a second sense amplifier.

5. The method according to claim 3, wherein the step of sensing sinus events comprises sensing any of:
   atrial events; or
   ventricular events.

6. The method according to claim 5, wherein the step of sensing ectopic events comprises sensing any of:
   premature atrial contractions (PACs), or
   premature ventricular contractions (PVCs).

7. The method according to claim 6, further including the step of determining an event interval by sampling at least two consecutive cardiac cycles to determine a time interval between two sensed events.

8. The method according to claim 7, further including the step of comparing the event interval to an average sinus interval measured between previously sensed sinus events, and, if the event interval is approximately equal to the average sinus interval, then confirming sinus event detection and sinus sensing threshold.

9. The method according to claim 8, further including the step of adjusting a sensitivity setting based on a sensing threshold determined for the detected sinus event.

10. The method according to claim 8, further including the step of comparing the event interval to the average sinus interval, and, if the event interval is a predetermined amount less than the average sinus interval, then confirming ectopic event detection and an ectopic sensing threshold.

11. The method according to claim 10, further including the step of setting the predetermined amount less than the average sinus interval to be equal to seventy percent of the average sinus interval.

12. The method according to claim 11, further including the step of adjusting a sensitivity setting based on a sensing threshold determined for the detected ectopic event.

13. The method according to claim 11, wherein, if the event interval is not equal to the average sinus interval and is not less than a predetermined percentage of the average sinus interval, re-determining the average sinus interval.

14. The method according to claim 1, further including repeating the steps of:
   determining sensing thresholds of sinus events; and
   sensing thresholds of ectopic events on a periodic basis.

15. The method according to claim 14, further including the step of storing a history of the sensing thresholds of the sinus events, the sensing threshold of the ectopic events, and the event intervals associated with sinus events and ectopic events.

16. The method according to claim 15, further including the step of displaying a histogram of stored sensing thresholds and stored event intervals.

17. The method according to claim 12, wherein, upon detecting a high incidence of premature ventricular contractions, differentiating between a premature ventricular contraction and an R-wave based on an undetected, conducted atrial event.

18. The method according to claim 17, wherein the step of differentiating between a premature ventricular contraction and an R-wave based the undetected; conducted atrial event comprises:
   setting an atrial sensitivity to a minimum numerical setting;
   re-classifying the premature ventricular contraction as an R-wave if an atrial event is sensed preceding the ventricular event; and
   confirming the ventricular event as a premature ventricular contraction if no atrial event is sensed preceding the ventricular event.

19. The method according to claim 18, further including the step of determining if the trial event is an atrial sinus event or an atrial ectopic event.

20. The method according to claim 19, wherein the step of determining if the atrial event is a sinus event or an ectopic event comprises the steps of:
   comparing the interval between the atrial event and the ventricular event to a previously measured average atrial-ventricular sinus interval (P-R interval);
   classifying the atrial event as a sinus event (P-wave) if the interval between the atrial event and the ventricular event equals the average atrial-ventricular sinus interval; and
   classifying the atrial event as a premature atrial contraction if the interval between the atrial event and the ventricular event is stable and does not equal the average atrial-ventricular sinus interval.

21. The method according to claim 20, further including the step of classifying the atrial event as a premature atrial contraction and the ventricular event a premature ventricular contraction if the interval between the atrial event and the ventricular event is substantially irregular.

22. The method according to claim 20, further including the step of determining the sensing threshold of the atrial event.

23. The method according to claim 22, further including the step of storing the sensing threshold of the atrial event and the coupling interval between the atrial event and the subsequent ventricular event in memory.

24. The method according to claim 22, wherein the step of determining the sensing threshold of the atrial event comprises the step of setting a sensing window relative in time to a preceding detected event, during which the atrial event will be sensed and all other atrial events occurring outside the sensing window will be ignored, while a sensitivity setting is adjusted until the sensing threshold of the atrial event is determined.

25. The method according to claim 1, further including the step of storing an electrogram of each ectopic event and each sinus event classified according to a sensing threshold.

26. The method according to claim 1, further including the step of storing an electrogram of each ectopic event and each sinus event classified according to average rate or coupling interval.

27. The method according to claim 1, further including the step of adjusting a sensitivity setting so that sinus events and one or more ectopic events are detected.

28. A cardiac stimulation device that differentiates between sinus events and ectopic events, comprising:
   electrodes that sense sinus events and ectopic events;
   a controller connected to the electrodes, that automatically determines sensing thresholds of the sinus events and of the ectopic events;
   a storage device that stores the sensing thresholds of the sinus events, the sensing thresholds of the ectopic events, and timing relationships that define sinus intervals and ectopic intervals;
   wherein the controller classifies a sensed cardiac event as a sinus event or an ectopic event based on the proximity of in amplitude of the cardiac event to any of the thresholds of the sinus events or the sensing thresholds of the ectopic events; and
   wherein the controller further classifies a sensed cardiac event as a sinus event or an ectopic event based on the proximity of the sensed cardiac event to a previous average cycle length in a corresponding cardiac chamber.

29. The device according to claim 28, wherein the controller adjusts a sensitivity setting until an event sensing threshold is determined, and determines the sinus event sensing thresholds on a rhythmic consistency of occurrence of the sensed events.

30. The device according to claim 29, wherein the controller automatically determines the sensing thresholds of the ectopic events by determining the ectopic event sensing thresholds on any one of:

a lack of rhythmic consistency of occurrence of sensed events, and a rhythmic consistency that is shorter in time than sinus event sensing.

31. The device according to claim 30, wherein the controller adjusts the sensitivity setting by maintaining a sensitivity setting of a first sense amplifier, while adjusting a sensitivity setting of a second sense amplifier.

32. The device according to claim 30, wherein the sinus events comprises any of atrial events, or ventricular events.

33. The device according to claim 32, wherein the ectopic events comprises any of: premature atrial contractions (PACs), or premature ventricular contractions (PVCs).

34. The device according to claim 28, further including a comparator that compares an event interval to an average sinus interval, and, if the event interval is a predetermined amount less than the average sinus interval, the controller confirms ectopic event detection and an ectopic sensing threshold.

35. A cardiac stimulation device that differentiates between sinus events and ectopic events, comprising:

means for sensing sinus events and ectopic events;

means for automatically determining sensing thresholds of the sinus events and of the ectopic events;

means for storing the sensing thresholds of the sinus events, the sensing thresholds of the ectopic events, and timing relationships that define sinus intervals and ectopic intervals;

means for classifying a sensed cardiac event as a sinus event or an ectopic event based on the proximity of an amplitude of the cardiac event to any of the sensing thresholds of the sinus events or the sensing thresholds of the ectopic events; and means for classifying a sensed cardiac event as a sinus event or an ectopic event based on the proximity of the sensed cardiac event to a previous average cycle length in a corresponding cardiac chamber.

36. The device according to claim 35, wherein the determining means adjusts a sensitivity setting until an event sensing threshold is determined, and determines the sinus event sensing thresholds on a rhythmic consistency of occurrence of the sensed events.

37. The device according to claim 36, wherein the determining means automatically determines the sensing thresholds of the ectopic events by determining the ectopic event sensing thresholds on any one of:

a lack of rhythmic consistency of occurrence of sensed events, and a rhythmic consistency that is shorter in time than sinus event sensing.

38. The device according to claim 37, wherein the determining means adjusts the sensitivity setting by maintaining a sensitivity setting of a first sense amplifier, while adjusting a sensitivity setting of a second sense amplifier.

39. The device according to claim 37, wherein the sinus events comprises any of atrial events, or ventricular events; and wherein the ectopic events comprises any of: premature atrial contractions (PACs), or premature ventricular contractions (PVCs).

40. The device according to claim 35, further including a comparator that compares an event interval to an average sinus interval, and, if the event interval is a predetermined amount less than the average sinus interval, the controller confirms ectopic event detection and an ectopic sensing threshold.

* * * * *